US012733870B2

(12) United States Patent
Zahalka et al.

(10) Patent No.: US 12,733,870 B2
(45) Date of Patent: Sep. 15, 2026

(54) METHOD OF MEASUREMENT OF KNEE STRENGTH CHARACTERISTICS IN PARTICULAR IN ISOKINETIC MOVEMENT AND DEVICE FOR CARRYING OUT THIS METHOD

(71) Applicant: Univerzita Karlova, Prague (CZ)

(72) Inventors: Frantisek Zahalka, Prague (CZ); Tomas Maly, Prague (CZ); Pavel Vodicka, Prague (CZ)

(73) Assignee: Univerzita Karlova, Prague (CZ)

( * ) Notice: Subject to any disclaimer, the term of this patent is extended or adjusted under 35 U.S.C. 154(b) by 855 days.

(21) Appl. No.: 17/754,716

(22) PCT Filed: Oct. 8, 2020

(86) PCT No.: PCT/CZ2020/050077
§ 371 (c)(1),
(2) Date: Apr. 8, 2022

(87) PCT Pub. No.: WO2021/068999
PCT Pub. Date: Apr. 15, 2021

(65) Prior Publication Data

US 2024/0074697 A1 Mar. 7, 2024

(51) Int. Cl.

*A61B 5/00* (2006.01)
*A61B 5/11* (2006.01)
*A61B 5/22* (2006.01)

(52) U.S. Cl.

CPC .......... *A61B 5/4585* (2013.01); *A61B 5/1121* (2013.01); *A61B 5/224* (2013.01); *A61B 5/702* (2013.01); *A61B 2503/10* (2013.01)

(58) Field of Classification Search

CPC ...... A61B 5/4585; A61B 5/1121; A61B 5/224
See application file for complete search history.

(56) References Cited

U.S. PATENT DOCUMENTS

| | | | | |
|---|---|---|---|---|
| 3,787,048 | A | 1/1974 | Bock | |
| 2015/0297128 | A1* | 10/2015 | Shield | A63B 23/0211 600/595 |
| 2021/0059592 | A1* | 3/2021 | Zahalka | A63B 24/0062 |

FOREIGN PATENT DOCUMENTS

| | | | |
|---|---|---|---|
| CZ | 307845 | B6 | 6/2019 |
| FR | 2600542 | A1 | 12/1987 |

(Continued)

OTHER PUBLICATIONS

"International Application No. PCT/CZ2020/050077, International Search Report and Written Opinion mailed Jan. 19, 2021", (Jan. 19, 2021), 10 pgs.

*Primary Examiner* — Daniel L Cerioni
(74) *Attorney, Agent, or Firm* — Schwegman Lundberg & Woessner, P.A.

(57) ABSTRACT

Method of measurement of knee strength characteristics is carried out in a manner that measured person in upright position leans against dynamometers with bearing surfaces (3) and movable arm (2) and starts transition to the sitting position, thus acting on the movable arm (2), which through connected sensor (21) of angular position monitors speed of change in angular position of the movable arm (2) and acts on dynamometers with bearing surfaces (3), which measure strength generated by measured person for each lower extremity individually, whereas sensor (21) of angular position and dynamometers transmit collected data to control unit, which evaluates speed of change in angular position of movable arm (2) and visualization equipment (4) shows to measured person actual and requested speed of change in angular position of movable arm (2) in a manner that measured person adjusts speed of transition from upright to sitting position to requested speed.

5 Claims, 2 Drawing Sheets

(56) References Cited

FOREIGN PATENT DOCUMENTS

| | | | |
|---|---|---|---|
| WO | WO-9111221 | A1 | 8/1991 |
| WO | WO-2019129317 | A1 | 7/2019 |
| WO | WO-2021068999 | A1 | 4/2021 |

* cited by examiner

[Fig. 1]
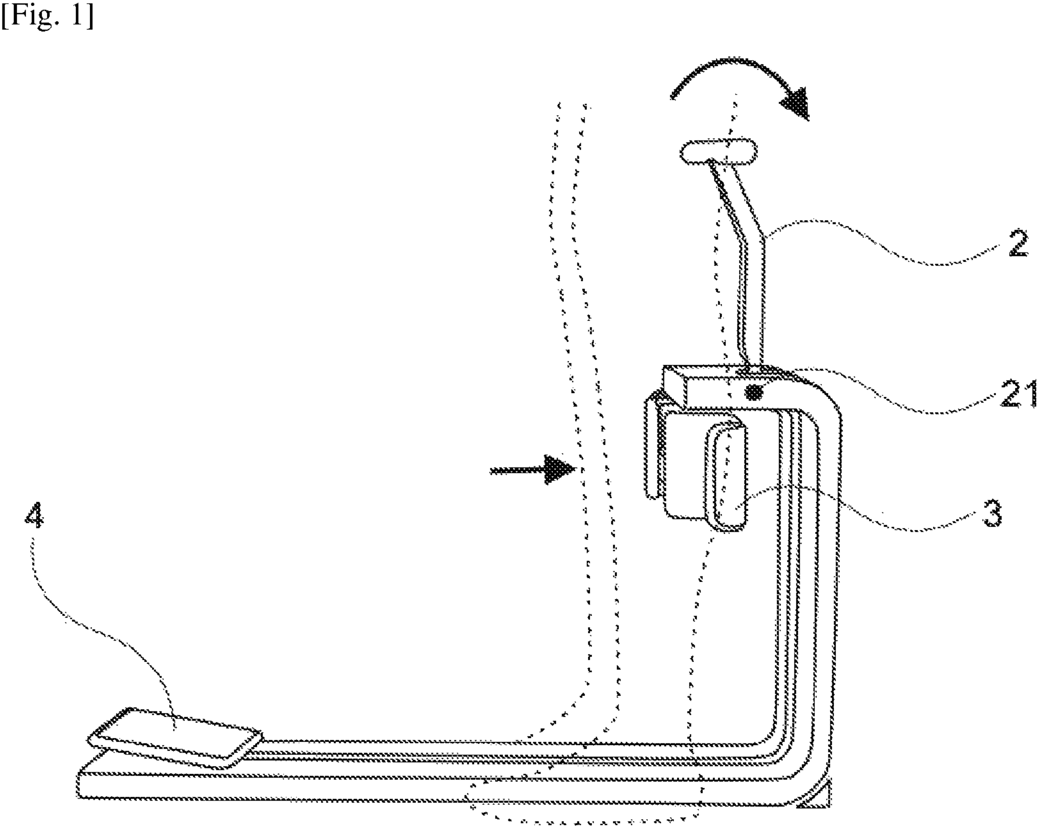
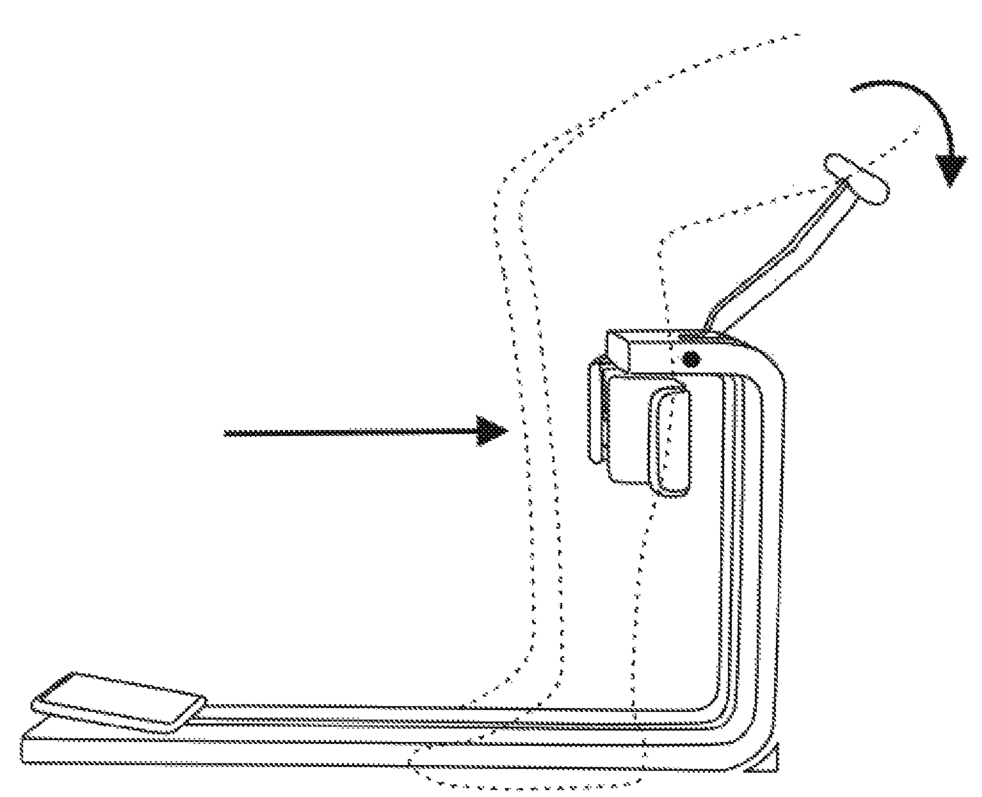

[Fig. 2]
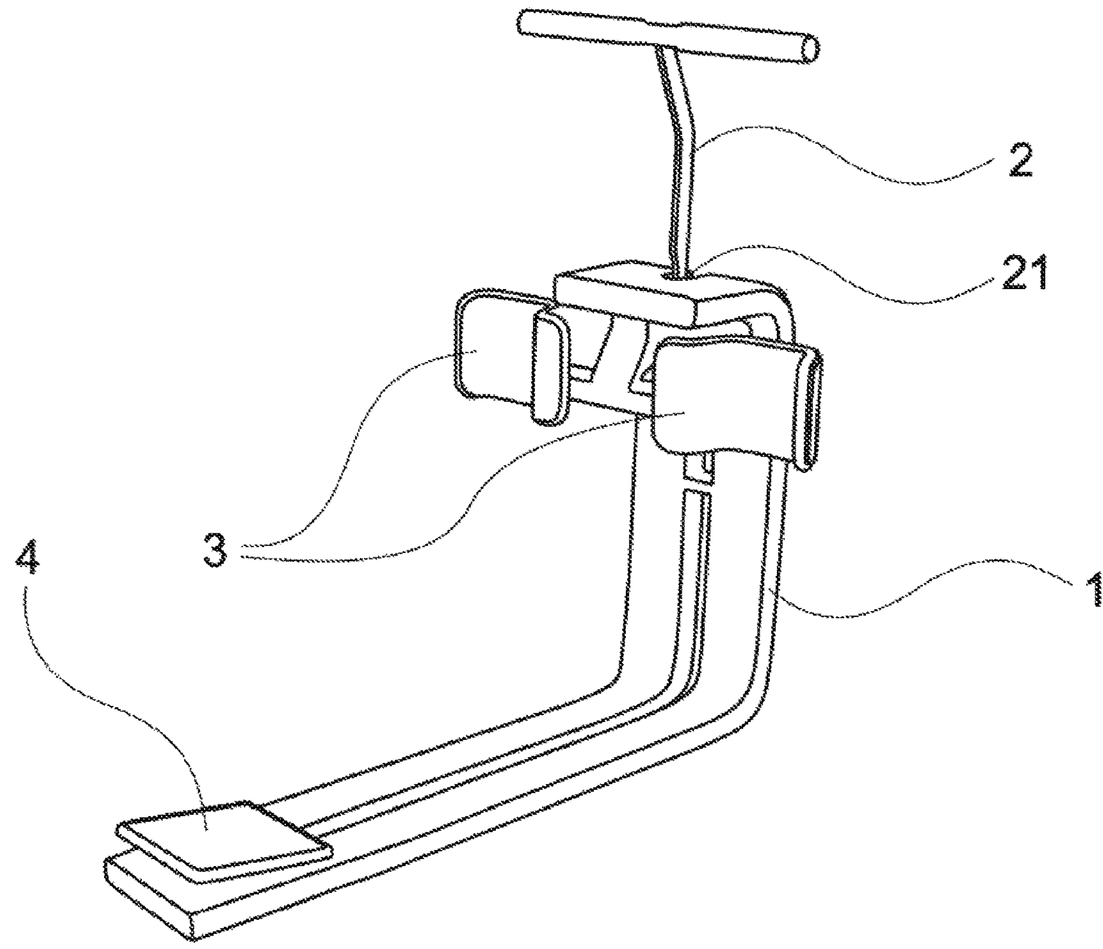
[Fig. 3]
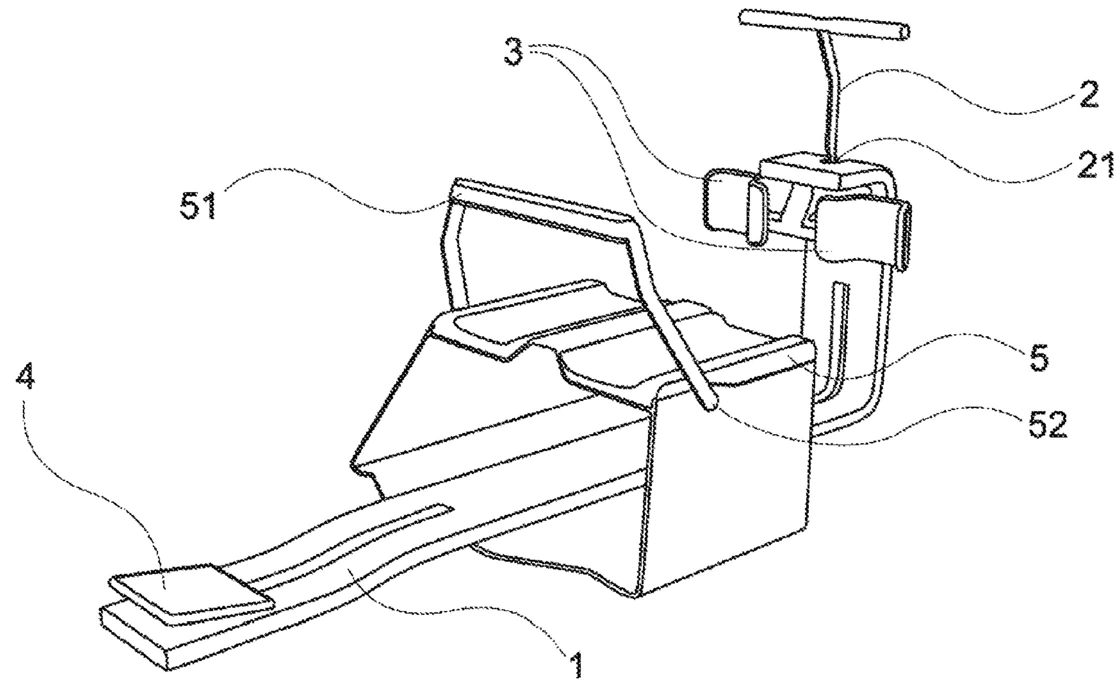

METHOD OF MEASUREMENT OF KNEE STRENGTH CHARACTERISTICS IN PARTICULAR IN ISOKINETIC MOVEMENT AND DEVICE FOR CARRYING OUT THIS METHOD

PRIORITY CLAIM TO RELATED APPLICATIONS

This application is a U.S. national stage filing under 35 U.S.C. § 371 from International Application No. PCT/CZ2020/050077, filed on 8 Oct. 2020, which claims priority to Czechia Application No. PV 2019-632, filed on 10 Oct. 2019. This application incorporates by reference the entirety of International Application No. PCT/CZ2020/050077 and its published version WO2021/068999 (published 15 Apr. 2021).

TECHNICAL FIELD

The invention falls within the scope of medical and gymnastic technologies, specifically devices and methods for kinetic energy measurement and training of muscles for sport or rehabilitation purposes.

BACKGROUND ART

Development of the invention relates to the method and device described in the document CZ307845, which enable measurement of lower extremity muscle strength, namely quadriceps femoris muscle, sartorius muscle, biceps femoris muscle, semitendinosus muscle, semimembranosus muscle and popliteus muscle, tibialis, toe extensor hallucis longus, thumb extensor hallucis longus, triceps surae, calf muscle long, and calf muscle short.

The device comprises of a mechanical unit measuring muscle strength and a control unit determining a pre-defined isokinetic movement. The mechanical unit comprises of a bearing surface for the knees of the measured person equipped with a sensor for sensing the angular position of the body of the measured person, an arm connected to the sensor of angular position, and at least one electric dynamometer to measure muscle pressure strength. The control unit comprises of a computer-controlled system with firmware to analyze data gathered from the electric dynamometer, sensor of angular position, and imaging equipment supplying optical instructions to the measured person in a manner so as this person keeps isokinetic movement or alternatively simultaneously also an audible device to supply acoustic instructions. The imaging equipment can be mounted perpendicularly to the axis of movement of the measured person or in the axis of movement for better sensorimotor guidance of the measured person. The control unit is also equipped with an interface to transfer data to the computer to allow their subsequent display and evaluation. Dynamometers, the sensor of angular position, and the control unit can be powered by an external power source or the device can be equipped with its own battery.

The method used by this device is employed in a manner that the measured person is in the kneeling position with the upright posture of both the trunk and thigh parts of lower extremities, and calf part of lower extremities perpendicular to them. The calf part of lower extremities is thus fixed by knees on the bearing surface and by ankles, leaning against dynamometers mounted above them. The measured person touches the arm of the sensor of angular position in the area of the upper part of the thigh. Measurement or exercise begins with the start of a forwarding angular movement of the measured person in such a manner that the angle of both the trunk and thigh part of lower extremities opens against the calf part of lower extremities. Gravitational force affects both the trunk and thigh part of lower extremities, thus orienting this part of the body towards the forwarding angular movement; strength of muscles of lower extremities counteracts this strength, measured during this movement by the dynamometers, against which the measured person leans by the ankles. The arm of the sensor of angular position copies the movement of the measured person in the forwarding angular movement; said movement, generated by the person, pushes the arm in the direction and speed of the movement of the measured person. The control unit evaluates the advancement of angular movement of the measured person on the basis of values supplied by the sensor of angular position monitoring the change in the speed of change in angular position, and based on these data the control unit displays the speed of change in angular movement on the imaging equipment and, at the same time, desired speed in such a manner to keep isokinetic mode. During the movement, the control unit continuously monitors the keeping of the isokinetic mode of the movement; if the defined deviation between actual and requested values is exceeded, the unit evaluates and records the course of values from the dynamometers and the sensor of angular position in their interaction. Thus, the described process allows measurement and evaluation of the course of movement both from the point of isokinetic demonstration of the movement and achieved individual limit values regarding the physical constitution of the measured person.

The shortcoming of such a device is its focus on the specific group of measured muscles, whereas data on the strength characteristics of the knee, muscle contraction of the quadriceps, eccentric muscle contraction of the knee extensors, concentric muscle contraction of the knee extensors, or isometric muscle contraction of the knee extensors cannot be obtained from results of such measurement.

Currently, the said shortcoming can be overcome only by the use of very complex devices, which are large and expensive. Such devices include, among others, the device described in the document WO9111221, where the measurement is made with the measured person in the sitting position; therefore, the device must be equipped with a large seat, considerably increasing the weight of the device and, consequently, restricting its mobility. The method of measurement using such device requires the measured person to do the concentric exercise with the contraction of the calf part of the lower extremity. Therefore, such or similar device must be equipped with electric motors or hydraulic or pneumatic system, working against the strength generated by muscles of the measured person.

The purpose of this invention is to propose a method which will reduce or eliminate the above-mentioned shortcoming while keeping the requested simplicity and self-service of the device, on which the said method will be employed.

SUMMARY OF INVENTION

Subject of the invention is the method of measurement of strength characteristics of the knee using a device which allows the collection of data on muscle contraction of the quadriceps, eccentric muscle contraction of the knee extensors, concentric muscle contraction of the knee extensors, or isometric muscle contraction of the knee extensors.

This method is applied in sub-steps, when the rear side of calves of the measured person in the upright posture leans against statically mounted dynamometers, with the rear part of thighs leaning against the movable arm; then, the measured person starts a transition to the sitting position, thus influencing the movable arm, which—by the connected sensor of angular position of the movable arm—monitors speed of change of angular position of the movable arm and, further, influences the dynamometers which measure the strength which the measured person generates individually for each lower extremity, whereas the sensor of angular position of the arm and dynamometers transmit collected information into the control unit, which evaluates the speed of change in angular position of the movable arm and informs the measured person about the actual and requested speed of change of angular position of the movable arm on the imaging equipment in a manner that the measured person will adjust the speed of transition from the upright posture to the sitting position to the requested speed.

Measurement or exercise done in this manner is advantageous to perform in the isokinetic mode as the isokinetic mode is the movement of muscles in the vicinity of their peak during the entire scope of movement in the joint and allows the full contraction in each point of the scope of movement. Especially for exercising, it is essential that the isokinetic movement means a maximum load of active muscles in the course of the entire scope of movement and allows to do a significantly more intensive work of muscles compared with the regular strength training as the muscle strength is not constant in the course of the movement.

Therefore, the said method allows measurement or exercise and evaluation of the course of movement of the measured person from the point of isokinetic demonstration of the movement and, at the same time, also from the point of achieved individual limit values regarding the physical constitution of the measured person.

In contrast to the state of the art, i.e. methods of measurement of strength characteristics of the knee, the invention especially differs in the different position of the body of the measured person, which is not in the sitting position with the fixed position of the trunk and thigh part of the lower extremity producing the movement only with the calf part of the lower extremity, but has the fixed calf part of the lower extremity, which leans against the dynamometers and makes the exercise by the movement of the thigh part of the lower extremity, where muscles of lower extremities generate pressure against the existing gravitational force.

The device used for the implementation of the described method comprises of the mechanical unit measuring muscle strength and the control unit determining the predefined isokinetic movement. The mechanical unit comprises of the frame, to which the movable arm is affixed, which is attached to the frame in its lower point in a manner that allows its rotation around the axis in this lower point. The sensor of angular position, reading data on the actual position of the movable arm, is attached to the movable arm in the axis of its rotation. Furthermore, dynamometers with the bearing surfaces located in the horizontal position for the calves of the measured person are attached to the frame. The control unit comprises of the computer-controlled system with firmware to analyze data gathered from the electric dynamometers, the sensor of angular position and further includes the imaging equipment supplying optical instructions to the measured person in a manner that this person keeps or adopts its movement to the pre-defined scenario of measurement or exercise, in particular isokinetic movement. The imaging equipment is fixed perpendicularly to the axis of movement of the measured person for better sensorimotor guidance of the measured person. The control unit is also equipped with the interface to transfer data to the computer to allow their subsequent display and evaluation.

The device can be preferably completed with the bearing surface connected to the frame, with another movable arm, to which another sensor of angular position is connected, whereas the said sensor of angular position is connected with the control unit. The dynamometers with bearing surfaces, in the point of their connection to the frame, will rotate from horizontal to vertical position, so that the measured person would lean against these bearing surfaces in the sitting position with thighs or ankles. The measured person starts measurement or exercise with the upright posture of both the trunk and thigh parts of lower extremities and the calf part of lower extremities perpendicular to them. The calf part of lower extremities is thus fixed by knees on the bearing surface and by ankles, leaning against the dynamometers mounted above them. The measured person touches the arm of the sensor of angular position in the area of the upper part of the thigh. Measurement or exercise begins with the start of the forwarding angular movement of the measured person in such manner that the angle of both the trunk and thigh part of lower extremities opens against the calf part of lower extremities. Gravitational force affects both the trunk and thigh part of lower extremities, thus orienting this part of the body towards the forwarding angular movement; strength of muscles of lower extremities counteracts this force and is measured in this movement by the dynamometers, against which the measured person leans by ankles.

In this configuration, the device allows measurement or exercise of other muscles of lower extremities, namely quadriceps femoris muscle, sartorius muscle, biceps femoris muscle, semitendinosus muscle, semimembranosus muscle and popliteus muscle, tibialis, toe extensor hallucis longus, thumb extensor hallucis longus, triceps surae, calf muscle long, and calf muscle short.

BRIEF DESCRIPTION OF DRAWINGS

FIG. 1 depicts the measured person in the position before and after the start of the method of measurement according to Example 1 with the help of the device according to Example 2.

FIG. 2 depicts an axonometric view of the device in the configuration according to Example 2.

FIG. 3 depicts an axonometric view of the device in the configuration according to Example 3.

DESCRIPTION OF EMBODIMENTS

Example 1

The method of measurement of strength characteristics of the knee using the device according to Example 2.

This method is performed in sub-steps where:

1) the measured person in the upright posture leans with the rear side of calves against statically mounted dynamometers with the bearing surfaces (3);
2) subsequently, the measured person leans against the movable arm (2) with the rear side of thighs;
3) subsequently, the measured person starts a transition into the sitting position;
4) by the change in its position, the measured person influences, with the rear side of its thighs or buttocks, the movable arm (2) in such a manner that the angular position of the movable arm (2) changes rotating around the axis in the lower point of the movable arm;

5) simultaneously with the change in its position, the measured person with the rear part of calves acts on dynamometers with the bearing surfaces (3), against which the measured person leans during the movement in order to change position;

6) change in the position of the movable arm (2) is monitored by the sensor of angular position (21) of the movable arm (2), connected to the axis of the lower point of the movable arm (2), monitoring the speed of change in the angular position of the movable arm (2), and transmits data on the change in the angular position of the movable arm, particularly the actual position of the movable arm (2) and speed of change in the angular position of the movable arm (2), to the control unit, recording said data;

7) strength generated by the rear part of calves of the measured person acting on the dynamometers with the bearing surfaces (3), is read by these dynamometers and data on strength and its change in time, which the measured person produces on the dynamometers with the bearing surfaces (3), is transmitted to the control unit, recording such data;

8) the imaging equipment (4) informs the measured person about the actual speed of change in the angular position of the movable arm and requested change in the speed of the angular position in a manner so that the measured person adjusts the speed of movement.

Example 2

Description of the preferred embodiments of the device according to the invention in the baseline option for the implementation of the method described in Example 1.

Such a device comprises of the frame (1) with connected vertically mounted movable arm (2). This movable arm (2) is mounted to the frame (1) in its lower point for its rotation around the axis located in this lower point. The sensor (21) of angular position for recording data on the actual position of the movable arm is connected to the movable arm (2) in the axis of its rotation. The dynamometers with the bearing surfaces (3) mounted in the vertical position for calves of the measured person are attached to the frame (1).

The device is also equipped with control unit which is connected to the sensor of angular position (21) and to the dynamometers with the bearing surfaces (3). The control unit comprises of computer-controlled system with firmware to analyze data gathered from the dynamometers (3) and from the sensor (2) of angular position, and furthermore the visualization equipment (4) for displaying optical instructions to the measured person for it to keep or modify performed movement. The visualization equipment (4) is placed perpendicularly to the axis of the movement of the measured person in a manner that the visualization equipment (4) is in the visual field of the measured person. In addition, the control unit is equipped with the interface to transfer data to the computer for their subsequent display and evaluation.

Example 3

Description of the preferred embodiments of the device in the combined variant including, in addition to the device described in Example 2, also components allowing measurement of strength of other muscles of lower extremities as well.

Such device comprises of the frame (1), to which the movable arm (2), connected to the frame (1) in its lower point for its rotation around the axis located in this lower point, is connected. The sensor (21) of angular position for recording data on the actual position of the movable arm is connected to the movable arm (2) in the axis of its rotation. The bearing surface (5) for knees is also connected to the frame (1); the movable arm (51) with the sensor of angular position (52) is connected to the bearing surface for the knees (5). Dynamometers with the bearing surfaces (3) are connected to the frame (1) in the pivot for the change in their position from the vertical, for pushing by calves of the standing measured person, to the horizontal, for pushing by ankles of the kneeling measured person.

The device is also equipped with the control unit, which is connected to the sensor (21) of angular position, to the sensor (52) of angular position, and to the dynamometers. The control unit comprises of the computer-controlled system with firmware to analyze data gathered from the dynamometers and the sensor (21) of angular position or the sensor (52) of angular position and, furthermore, the visualization equipment (4) for displaying optical instructions to the measured person for it to keep or modify performed movement. The visualization equipment (4) is placed perpendicularly to the axis of the movement of the measured person in a manner that the visualization equipment (4) is in the visual field of the measured person. In addition, the control unit is equipped with the interface to transfer data to the computer for their subsequent display and evaluation.

INDUSTRIAL APPLICABILITY

The method of measurement of strength characteristics of the knee and the device for implementation of this method is primarily applicable to diagnostic or training purposes, namely for sportsmen or convalescent patients.

The invention claimed is:

1. A method for measurement of knee strength characteristics, the method comprising:

providing an apparatus including vertically mounted dynamometers with bearing surfaces and a movable arm connected to a sensor of angular position;

placing a measured person in an upright position with a rear side of calves against the dynamometers with the bearing surfaces;

leaning a rear side of thighs of the measured person against the movable arm;

starting a transition of the measured person from the upright position to a sitting position:

sensing, during the transition from the upright position to the sitting position, a speed of change in angular position of the movable arm using the connected sensor of angular position when the measured person leans with the calves against the dynamometers and the thighs against the movable arm and transitions from an upright position to a sitting position;

sensing energy strength generated by the measured person individually for each lower extremity during the transition using the dynamometers;

transmitting collected data from the sensor of angular position and the dynamometers to a control unit;

recording the data from the sensor of angular position and the dynamometers by the control unit;

determining an actual speed of change in angular position of the movable arm using the control unit;

determining whether the measured person is performing a movement from the upright position to the sitting position at a constant speed of change in angular position of the movable arm. or whether defined deviations between actual and requested values of the speed of change in angular position of the movable arm are exceeded; and displaying, by the control unit, on a visualization equipment, information provided by the control unit comprising the actual speed and the requested speed of change in angular position of the movable arm and providing instructions to the measured person to adjust the actual speed to the requested speed of the transition from the upright position to the sitting position.

2. The method of claim 1, further comprising:

playing audible instructions to the measured person to adjust to the requested speed of the transition from the upright position to the sitting position.

3. The method of claim 1, further comprising:

storing the collected data in a memory.

4. The method of claim 1, further comprising:

using firmware of the control unit to analyze data received from the dynamometers and the sensor of angular position.

5. The method of claim 1, further comprising:

transferring, by the control unit, data to a remote device for subsequent evaluation.

* * * * *